United States Patent [19]

DeLonzor

[11] Patent Number: 5,246,003
[45] Date of Patent: Sep. 21, 1993

[54] DISPOSABLE PULSE OXIMETER SENSOR

[75] Inventor: Russell DeLonzor, Union City, Calif.

[73] Assignee: Nellcor Incorporated, Hayward, Calif.

[21] Appl. No.: 838,565

[22] Filed: Feb. 19, 1992

Related U.S. Application Data

[63] Continuation-in-part of Ser. No. 751,405, Aug. 28, 1991, abandoned.

[51] Int. Cl.$^5$ .............................................. A61B 5/00
[52] U.S. Cl. ..................................... 128/633; 128/666
[58] Field of Search ................... 439/67, 77, 492, 499, 439/495, 909; 128/633, 664–666; 356/41

[56] References Cited

U.S. PATENT DOCUMENTS

| | | | |
|---|---|---|---|
| 3,617,374 | 11/1971 | Hodson et al. | 346/76 PH |
| 4,621,643 | 11/1986 | New, Jr. et al. | |
| 4,644,092 | 2/1987 | Gentry | 174/117 FF |
| 4,653,501 | 3/1987 | Cartmell et al. | 128/640 |
| 4,685,464 | 8/1987 | Goldberger et al. | |
| 4,825,872 | 5/1989 | Tan et al. | |
| 4,848,335 | 7/1989 | Manes | 128/908 |
| 4,863,757 | 9/1989 | Durand | |
| 4,915,116 | 4/1990 | Hasebe et al. | |
| 4,928,691 | 5/1990 | Nicolson et al. | 128/633 |
| 4,960,614 | 10/1990 | Durand | |
| 4,964,408 | 10/1990 | Hink et al. | 128/633 |
| 4,974,591 | 12/1990 | Awazu et al. | |
| 5,006,397 | 4/1991 | Durand | |
| 5,036,128 | 7/1991 | Durand | |
| 5,047,260 | 9/1991 | Durand | |
| 5,054,488 | 10/1991 | Muz | |
| 5,061,551 | 10/1991 | Durand | |
| 5,069,213 | 12/1991 | Polczynski | |

FOREIGN PATENT DOCUMENTS

| | | | |
|---|---|---|---|
| 0284943 | 5/1988 | European Pat. Off. | |
| 2348992 | 4/1974 | Fed. Rep. of Germany | 439/495 |
| 8909566 | 10/1989 | World Int. Prop. O. | 128/633 |

*Primary Examiner*—Lee S. Cohen
*Assistant Examiner*—Robert L. Nasser, Jr.
*Attorney, Agent, or Firm*—Townsend and Townsend Khourie and Crew

[57] ABSTRACT

A conformable sensor which uses a flexible substrate, preferably a polyester strip is disclosed. The emitter and detector are mounted on one portion of the strip with conductive traces connecting to them. The second portion of the strip is folded over to cover the emitter and detector and traces, with openings for the emitter and detector. A conductive coating is applied to the strip to provide shielding from electromagnetic interference. Preferably, a second portion of the strip, which folds over the first portion, also has a Faraday shield covering the opening over the detector.

26 Claims, 3 Drawing Sheets

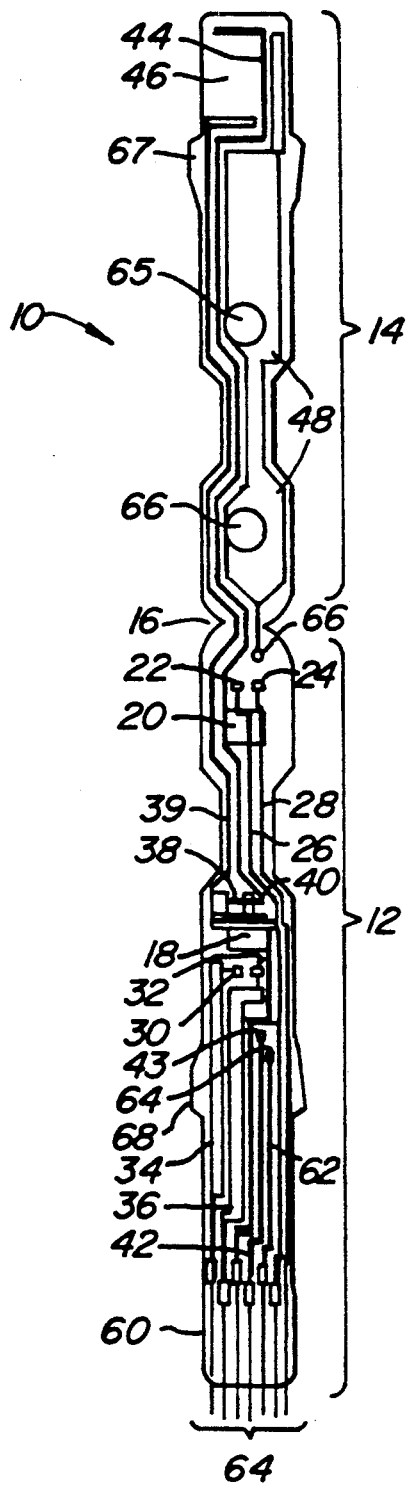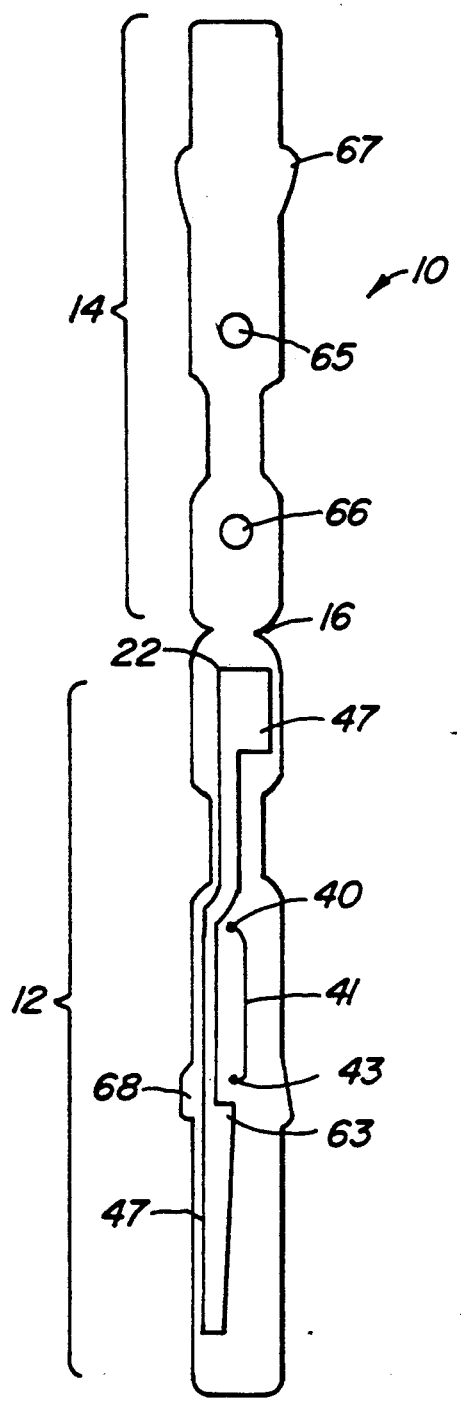
FIG. 1.
FIG. 2.

DISPOSABLE PULSE OXIMETER SENSOR

This application is a continuation-in-part of Ser. No. 751,405, filed Aug. 28, 1991; now abandoned.

BACKGROUND

This invention relates to sensors for use with noninvasive pulse monitors such as plethysmographs or pulse oximeters.

A plethysmograph is a pulse monitor. The plethysmograph sensor shines light into the patient's tissue, and the light transmitted through the tissue is received by a photodetector. The photodetector generates electrical signals corresponding to the transmitted light levels and transmits the signals to a monitor for processing. Arterial blood will absorb some of the light, with more light being absorbed when there is more blood. Thus, changes in the amount of transmitted light are related to pulses of arterial blood in the illuminated tissue.

A pulse oximeter is a device for noninvasively determining the oxygen saturation of arterial blood. The pulse oximeter sensor shines light at two different wavelengths (one in the red range, the other in the infrared range) through a portion of the patient's blood-perfused tissue. The red and infrared light transmitted through the tissue is detected by a photodetector. The amount of light absorbed varies with the amount of oxygen in the blood, and varies differently for red and infrared light. The pulse oximeter monitor computes blood oxygen saturation based on the changes in the two detected light levels between two points in time.

There are several types of sensors for plethysmographs and pulse oximeters. One is a surface sensor in which the light emitter and the photodetector are mounted on the same sensor face. The sensor is attached to the patient with both the light emitter and the detector on the same side of the patient's appendage (e.g., on the patient's forehead). This type of sensor detects light reflected back from the tissue, rather than light transmitted through an appendage. The signal detected will thus be weaker in most cases. The sensor is typically attached with a strap, headband or tape over the sensor, or an adhesive pad between the sensor and the skin.

Another type of sensor is a clamp design, such as that described in U.S. Pat. No. 4,685,464. The durable sensor described in that patent has deformable pads creating conforming tissue contacting surfaces to which the emitters and photodetector are secured. The deformable pads are disposed in a hinged rigid housing that clips on the patient like a clothes pin. This relies on a clamping force to secure the sensor to the patient. The force of the sensor against the patient's tissue could reduce the flow of blood to that region. This exsanguination of the tissue beneath the sensor adversely affects pulse detection and analysis by suppressing the pulse in that portion of the tissue. As a result, the sensor site must typically be checked or moved every four hours to insure adequate perfusion. Because of its relatively large mass, however, the clamp design is more susceptible to signal-distorting motion artifact. i.e., differential motion between the sensor and the patient.

A third sensor design is described in U.S. Pat. No. 4,830,014. The conformable sensor described in that patent has emitters and a photodetector mounted in the same side of a flexible web. The web wraps around a portion of the patient's tissue (such as a finger) so that the light from the emitters must travel through the tissue before reaching the detector. The web attaches to the skin with an adhesive surface on the emitter and detector side of the web. Because of its relatively low mass and the adhesive, this sensor adheres closely to the patient's skin and minimizes the effects of motion artifact. In addition, its flexibility and use of adhesive to secure it minimizes the exsanguination caused by rigid sensors. Thus the sensor site typically only needs to be checked every eight hours.

One problem with such a conformable sensor is that of electromagnetic and photic interference with the detector. In the clamp-type of sensor, a Faraday shield, which is a grid of wires, covers the emitter to block out electromagnetic interference. In addition, shielded cabling is used to prevent interference with the conductive lines carrying the signal from the detector. The use of such shielded cabling to connect up to the detector on a conformable sensor makes the sensor bulky and more expensive.

In one type of sensor, disclosed in U.S. Pat. No. 4,621,643, a coding resistor is attached to the probe to indicate the wavelength of light emitted by the particular emitter. The selecting and attaching of such a coding resistor to a conformable sensor makes the manufacturing process difficult and expensive.

It is desirable to have an inexpensive conformable sensor which is easy to manufacture and provides appropriate shielding and a coding resistor.

SUMMARY OF THE INVENTION

The present invention provides a conformable sensor which uses a flexible substrate, preferably a polyester strip. The emitter and detector are mounted on one portion of the strip with conductive traces connecting to them. The second portion of the strip is folded over to cover the emitter and detector and traces, with openings for the emitter and detector. A conductive coating is applied to the strip to provide shielding from electromagnetic interference. In certain embodiments, a second portion of the strip, which folds over the first portion, may also have a Faraday shield covering the opening over the detector.

The Faraday shield is preferably connected to the conductive coating on the first portion of the strip through a conductive via. The conductive coating is in turn connected to the ground trace on the first portion of the strip through another conductive via. The coating is deposited using the same process which produces the conductive traces. This makes the sensor very easy and inexpensive to manufacture, giving a very good disposable sensor.

A unique connector is provided which operates like a belt buckle. One end of the conductive strip having the conductive traces is passed through slots in a plug and then folded back over a central portion and secured. The plug is then forced into a socket which has an opening with pins extending downward to contact the conductive traces. The folded, flexible polyester substrate forms a spring action to press the contacts against the pins.

The present invention also provides a coding resistor which has a value corresponding to the actual wavelength of the particular emitter used. The coding resistor can be a ceramic resistor bonded to traces on the substrate or a laser trimmable resistor which is deposited on the substrate along with the conductive traces. Thus, it can easily be trimmed to the appropriate value during the manufacturing process.

For a fuller understanding of the nature and advantages of the invention, reference should be made to the ensuing detailed description taken in conjunction with the accompanying drawings.

BRIEF DESCRIPTION OF THE DRAWINGS

FIG. 1 is view of the front of the substrate of a sensor according to the preferred embodiment of this invention;

FIG. 2 is view of the back of the substrate of FIG. 1;

DETAILED DESCRIPTION OF THE PREFERRED EMBODIMENTS

Figure 3:
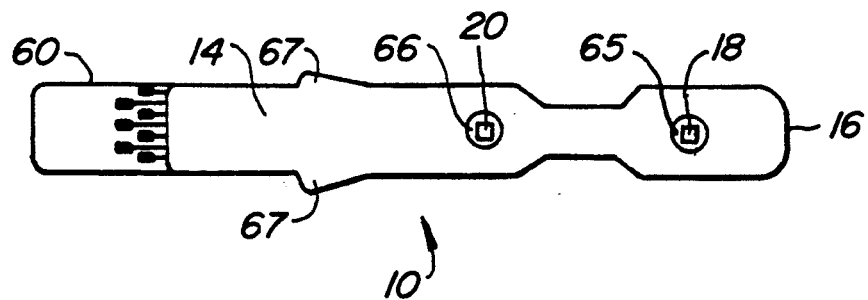
FIG. 3 is a view of a folded substrate according to the preferred embodiment.

FIG. 1 is an elevational view of the front, and FIG. 2 is an elevational view of the back, of the substrate of a sensor according to the preferred embodiment of this invention. Generally, the electrooptical sensor components described below are deposited or mounted on a polyester substrate tape 10 in a configuration dictated by this invention. Poly-Flex Circuits, Inc., of Cranston, Rhode Island, is the preferred vendor for the substrate and for the conductive trace deposition and component mounting processes.

Polyester substrate 10 has a first portion 12 and a second portion 14 which is folded over portion 12 from a hinge point 16 In the preferred embodiment, polyester substrate 10 is approximately 5 mils thick. In any event, it should be greater than approximately 3 mils to avoid capacitive coupling between the grounded shield and the other traces.

The sensor's photoemitter 18 and photodetector 20 (shown in FIG. 1 as phantom rectangles) are mounted on portion 12 of substrate 10. The leads of photodetector 20 are bonded to conductive traces 26 and 28 at points 22 and 24, respectively, preferably using Poly-Flex Circuits, Inc., Poly-Solder "F" conductive adhesive. The leads of photoemitter 18 are connected to traces 34 and 36 at points 30 and 32, respectively, in the same manner. Epoxy is placed over both sets of leads, and a dielectric coating is applied to the entire circuit.

A coding resistor 38 is connected between trace 39 on the front of substrate portion 12 and, via a conductive through-hole 40, a trace 41 on the back side of substrate portion 12. Trace 41 connects to trace 42 on the front side of substrate portion 12 via through-hole 43. The value of resistor 38 is used to indicate the wavelength of light emitted by photoemitter 18 as discussed in U.S. Pat. No. 4,621,643.

The circuit shown in FIGS. 1 and 2 also contains a feature used in an alternative embodiment. Trace 39 and a trace 44 bound an open area 46 on the front of substrate portion 14. Trace 44 communicates with trace 41 on the back of substrate 10 via through-hole 40. A printed resistor may be formed in area 46 by depositing a somewhat less conductive ink. The value of the printed resistor may be adjusted by making a lateral cut, possibly followed by a longitudinal cut, in the inked area 46. The cut may be made by a laser or by any other suitable cutting means. This printed resistor may be used in place of discrete resistor 38. Other shaped cuts may be used as well.

In yet another alternative embodiment, a discrete transistor may be used in series with a printed resistor. A circuit other than the circuit shown in FIG. 1 must be used, of course, to provide the series resistor relationship.

In order to minimize the effects of ambient electromagetic noise on the signal generated by the sensor, shielding is provided in particularly sensitive portions of the sensor. Specifically, conductive coating areas 47 and 48 are provided on the back of substrate portion 12 and on the front of substrate portion 14, respectively. The conductive coating is preferably silver ink of the same type used to form the traces for the electrical connections. It should be also be noted that if a transparent substrate were used in place of the preferred opaque substrate 10, the conductive coating areas would provide some shielding from the effects of ambient light as well.

Traces 26, 28, 34, 36, 39, and 42 extend to a connector area 60 on the end of the front side of substrate portion 12. A grounding trace 62 also extends from the connector area 60. Grounding trace 62 connects to conductive coating area 47 via conductive through-hole 63, and conductive coating area 47 connects to conductive coating area 48 via a conductive through-hole 66. All traces end in widened contact pads 64 for connection to the sensor's cable, as discussed below.

After the optical components and coding resistor have been mounted, substrate 10 is folded about hinge 16 so that the fronts of substrate portions 12 and 14 meet. Folding at hinge 16 ensures that holes 65 and 66 will line up with photoemitter 18 and photodetector 20, respectively, as shown in FIG. 3. Folding at hinge 16 also makes tabs 67 on substrate portion 14 line up with tabs 68 on substrate portion 12. In addition, contact pads 64 in connector area 60 remain uncovered when substrate 10 is folded.

Figure 5:
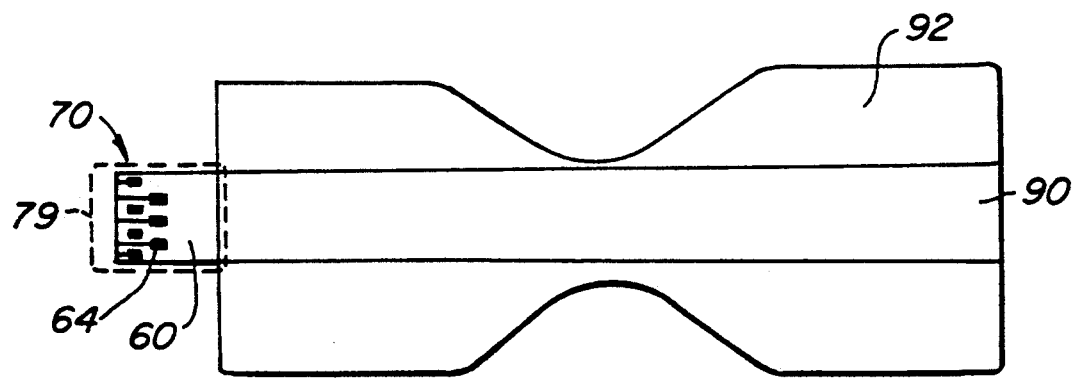
FIG. 5 is a view of the folded substrate inside a bandage.
Figure 4:
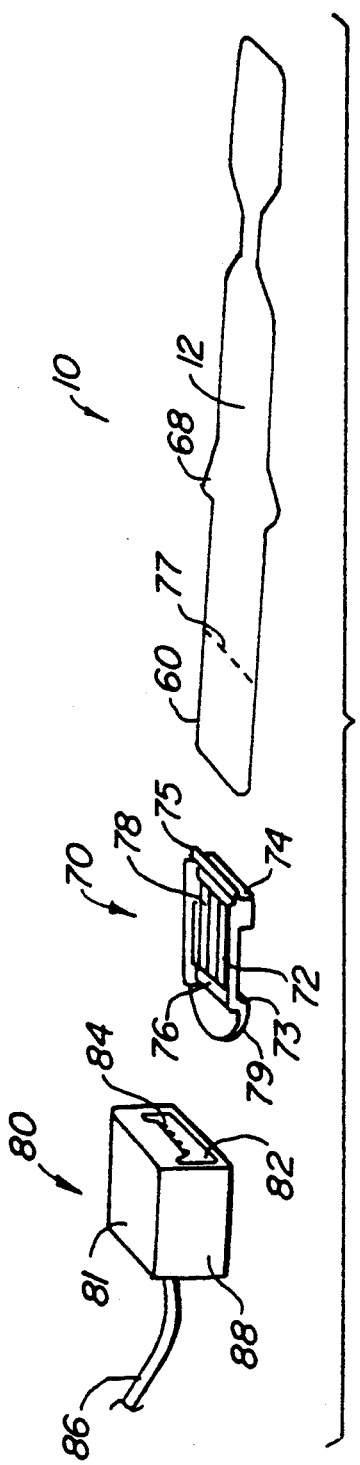
FIG. 4 is an exploded view of the folded substrate, connector plug and cable connector.

A connector plug 70 for attaching to the end of the substrate and a cable connector are shown in FIG. 4. Connector area 60 of substrate 10 is inserted beneath bar 75 into slot 74. Connector area 60 passes through slot 76 and is folded upward and backward about dotted line 77 to pass over central support 72, then passes through back through slot 74. Insertion continues until tabs 67 and 68 meet plug 70. The contact pads 64 are then disposed over central support 72 as shown in FIG. 5.

Connector plug 70 can then be inserted into an opening 82 in a connector 80. As plug is inserted, contact pads 64 (which are now on the top of plug 70) will come into contact with a number of pins 84. Pins 84 communicate with conductors in cable 86, which is connected to the pulse oximeter monitor.

Pins 84 line up with grooves 78 formed on the top of central support 72. As plug 70 is inserted into connector 80, pins 84 press substrate 10 down into grooves 78. The resiliency of the substrate material ensures good electrical contact between contact pads 64 and pins 84. In addition, because of the way the substrate is bent about plug 70, connector area 60 will be bowed upward, providing a spring action due to its resiliency. Thus, when plug 70 in inserted into slot 82, the spring action will force contact pads 64 up against pins.

To ensure that plug 70 is inserted into cable connector 80 in the proper orientation, a pair of grooves 90 are formed in slot 82 that mate with bars 72 on plug 70. In addition, when plug 70 has been inserted all the way into connector 80, the resilient spring action of the folded substrate will force plug 70 downward causing edge 73 of the plug to move downward and catch on the backside of connector 80, holding it in place.

A conductive shield is provided on cable connector face 88, face 89 and the face opposite face 88. This shield communicates with a ground signal in cable 86.

FIG. 5 is a top view of the assembled sensor. After mounting plug 70 on substrate 10, a white polyethylene covering 90 is wrapped about folded substrate 10. A pair of holes in covering 90 line up with holes 65 and 66 on the bottom side of the view shown in FIG. 5 to expose the optical components. The now covered substrate 10 is mounted on a clear, permeable adhesive web 92.

Figure 7:
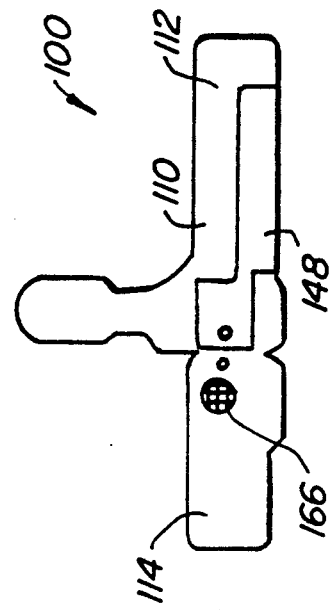
FIG. 7 is a view of the back of the substrate of the sensor of FIG. 6.
Figure 6:
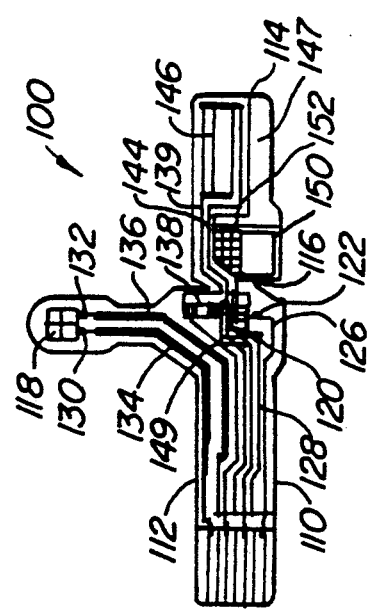
FIG. 6 is a view of the front of the substrate of a sensor according to an alternative embodiment.

FIG. 6 is an elevational view of the front, and FIG. 7 is an elevational view of the back, of an alternate embodiment of the present invention for a neo-natal sensor 100. Substrate 110 is divided into two portions by a hinge area 116: an L-shaped portion 112 and a cover portion 114. A second portion of the substrate 104 folds over a first portion 106. A photoemitter 118 and a photodetector 120 (shown in phantom in FIG. 6) are mounted on substrate portion 112 in the same manner as in the previous embodiment. The leads of photodetector 120 are bonded to conductive traces 126 and 128 at points 122 and 124, respectively. The leads of photoemitter 118 are bonded to traces 134 and 136 at points 130 and 132, respectively. Epoxy is placed over both sets of leads, and the entire circuit is covered with a dielectric coating.

A coding resistor 138 is connected between trace 139 and trace 144. Alternatively, a printed resistor may be formed in area 146.

Conductive coating areas 147 and 149 are provided on the front of substrate 110 and conductive coating area 148 is provided on the back for shielding. Areas 147, 148 and 149 are connected to a ground signal via trace 162. Additional shielding is provided with a thin copper plate 150 having a Faraday shield portion 152 covering hole 166. Plate 150 is bonded to conductive area 147 in the same manner as the optical components and discrete resistor.

Traces 126, 128, 134, 136, 139, 142 and 162 extend into a connector area 160 of substrate 110. Substrate 110 is folded about hinge 116 so that hole 166 leaves photodetector 120 exposed through Faraday shield 152 A connector plug is attached to substrate 110 for connection to a cable connector as in the earlier version. The folded substrate is attached to an adhesive bandage similar in shape and function to the bandage used in the Nellcor Incorporated OXISENSOR N-25 product.

As will be understood by those familiar with the art, the present invention may be embodied in other specific forms without departing from the spirit or essential characteristics thereof. Accordingly, the disclosure of the preferred embodiment of the invention is intended to be illustrative, but not limiting, of the scope of the invention which is set forth in the following claims.

What is claimed is:

1. A non-invasive, electrooptical sensor for removable attachment to the skin of a patient, comprising:
    a flexible substrate;
    a light emitter mounted on a first portion of the substrate;
    a light detector mounted on said first portion of the substrate;
    a plurality of conductive lines on the first portion of the substrate connected to the light emitter and the light detector;
    a second portion of the substrate which is folded over to cover the first portion of the substrate, with openings in the second portion over the light emitter and the light detector; and
    a flexible conductive layer on a surface of the second portion of the substrate covering a portion of said lines connected to the light detector.

2. The sensor of claim 1 wherein the substrate is polyester.

3. The sensor of claim 1 wherein said conductive layer is conductive ink.

4. The sensor of claim 1 wherein said conductive lines are silver traces.

5. The sensor of claim 1 further comprising a Faraday shield mounted on said second portion of said substrate above said light detector.

6. The sensor of claim 1 further comprising a coding resistor coupled to one of said conductive lines.

7. The sensor of claim 6 wherein said coding resistor is formed from conductive ink.

8. The sensor of claim 1 further comprising a rigid plug coupled to one end of said first portion of the flexible substrate.

9. The sensor of claim 8 further comprising electrical contacts on said substrate connected to said conductive lines, wherein said plug has a central member with slots on either side, said first portion of the flexible substrate passing through said slots on a first side of said central member and then bending back across a second side of said central member, exposing the electrical contacts, said contacts facing away from said central member.

10. The sensor of claim 1 wherein said conductive layer is on an inside surface of said second portion of said substrate when folded over said first portion of said substrate.

11. The sensor of claim 10 further comprising a second conductive layer on an outside surface of said first portion of said substrate, said light emitter, light detector and conductive lines being on an inside surface of said first portion of said substrate.

12. The sensor of claim 11 further comprising:
    a shield conductive line extending from said first mentioned conductive layer to said first portion of said substrate; and
    a conductive through-hole connecting said shield conductive line to said second conductive layer.

13. The sensor of claim 1 wherein said second portion is shorter than said first portion such that said conductive lines are exposed where not covered by said second portion when folded over.

14. The sensor of claim 13 further comprising electrical contacts connected to said conductive lines where said conductive lines are not covered by said second portion when folded over.

15. The sensor of claim 1 further comprising:
    second conductive lines extending from said first portion to said second portion; and
    an electrical component coupled between said second conductive lines.

16. The sensor of claim 15 wherein said electrical component is a coding resistor.

17. A non-invasive, electrooptical sensor for removable attachment to the skin of a patient, comprising:
    a first flexible substrate;
    a light emitter mounted on the first substrate;

a light detector mounted on the first substrate;

a plurality of conductive lines on the first substrate connected to the light emitter and the light detector;

a plurality of electrical contacts on said first substrate connected to said conductive lines;

a second substrate covering portions of the first substrate with openings over the light emitter and the light detector;

a flexible conductive layer on a surface of the second substrate covering a portion of said lines connected to the light detector;

a rigid plug coupled to one end of said first flexible substrate, said plug having a central member with slots on either side, said first flexible substrate passing through said slots on a first side of said central member and then bending back across a second side of said central member, exposing said electrical contacts, said contacts facing away from said member; and a socket for receiving said plug, said socket having a slot for receiving said plug with a plurality of pins extending into said socket for engaging with said electrical contacts, said pins being electrically connected to wires extending out of said socket.

18. The sensor of claim 17 wherein said slots are positioned so that said first substrate bows outward on one side of said central member, such that when said plug is inserted into said socket, a bowed portion of said first substrate forces said electrical contacts into contact with said pins with a spring force.

19. The sensor of claim 17 wherein said plug has at least one protruding member mating with a corresponding slot in said socket to prevent insertion except in a desired orientation.

20. A non-invasive, electrooptical sensor for removable attachment to the skin of a patient, comprising:

a flexible substrate having a second portion folded over to cover a first portion;

a light emitter mounted on said first portion;

a light detector mounted on said first portion;

a plurality of conductive traces on said first portion connecting to said light emitter and light detector;

said second portion of said substrate having openings over said light emitter and light detector; and a conductive ink on an outside surface of said substrate covering areas of said substrate over a portion of said conductive traces.

21. The sensor of claim 20 further comprising a coding resistor coupled to one of said conductive trace 22. The sensor of claim 21 wherein said coding resistor is formed from conductive ink.

23. A non-invasive, electrooptical sensor for able attachment to the skin of a patient, comprising:

a flexible substrate;

a light emitter mounted on a first portion of said substrate;

a plurality or conductive lines on said first portion of said substrate connecting to said light emitter and light detector;

a plurality of electrical contacts on said first portion of said substrate connected to said conductive lines;

a second portion of said substrate which is folded over to cover said first portion of said substrate with openings in said second portion over said light emitter and light detector; and a rigid plug coupled to one end of said flexible substrate, said plug having a central member with slots on either side, said flexible substrate passing through said slots on a first side of said central member and then bending back across a second side of said central member, exposing said electrical contacts, said contacts facing away from said central member.

24. A non-invasive, electrooptical sensor for removable attachment to the skin of a patient, comprising:

a first flexible substrate;

a light emitter mounted on said first substrate;

a light detector mounted on said first substrate;

a plurality of conductive lines on said first substrate connecting to said light emitter and light detector;

a plurality of electrical contacts on said first substrate connected to said conductive lines;

a second substrate covering portions of said first substrate with openings over said light emitter and light detector;

a rigid plug coupled to one end of said first flexible substrate, said plug having a central member with slots on either side, said first flexible substrate passing through said slots on a first side of said central member and then bending back across a second side of said central member, exposing said electrical contacts, said contacts facing away from said central member; and a socket for receiving said plug, said socket having a slot receiving said plug with a plurality of pins extending into said socket engaging with said electrical contacts, said pins being electrically connected to wires extending out of said socket.

25. The sensor of claim 24 wherein said slots are positioned so that said first substrate bows outward on one side of said central member, such that when said plug is inserted into said socket, a bowed portion of said first substrate forces said electrical contacts into contact with said pins with a spring force.

26. The sensor of claim 24 wherein said plug has at least one protruding member mating with a corresponding slot in said socket to prevent insertion except in a desired orientation.

* * * * *